US006407297B1

(12) United States Patent
Ewing

(10) Patent No.: US 6,407,297 B1
(45) Date of Patent: Jun. 18, 2002

(54) PREPARATION OF FLUORINE-CONTAINING ORGANIC COMPOUNDS

(75) Inventor: Paul Nicholas Ewing, Cheshire (GB)

(73) Assignee: Ineos Fluor Holdings Limited, Southampton (GB)

(*) Notice: Subject to any disclaimer, the term of this patent is extended or adjusted under 35 U.S.C. 154(b) by 0 days.

(21) Appl. No.: 09/555,121

(22) PCT Filed: Nov. 12, 1998

(86) PCT No.: PCT/GB98/03408

§ 371 (c)(1),
(2), (4) Date: Jul. 13, 2000

(87) PCT Pub. No.: WO99/26907

PCT Pub. Date: Jun. 3, 1999

Related U.S. Application Data

(60) Provisional application No. 60/066,836, filed on Nov. 25, 1997.

(30) Foreign Application Priority Data

Nov. 25, 1997 (GB) .............................................. 9724831

(51) Int. Cl.[7] .............................................. C07C 17/38
(52) U.S. Cl. ....................................................... 570/178
(58) Field of Search ......................................... 570/178

(56) References Cited

U.S. PATENT DOCUMENTS 5,475,169 A    12/1995   Hopp et al.

FOREIGN PATENT DOCUMENTS

| DE | 27 12732 C2 | 9/1978 |
|----|-------------|--------|
| EP | 0 467 531   | 1/1992 |
| GB | 902590      | 8/1962 |
| GB | 1 568 020   | 5/1980 |
| GB | 2 277 087   | 10/1994 |
| WO | WO 95/32935 | 12/1995 |
| WO | WO 96/00243 | 1/1996 |
| WO | WO 97/11042 | 3/1997 |
| WO | WO 97/13179 | 4/1997 |

Primary Examiner—Alan Siegel
(74) Attorney, Agent, or Firm—Cook, Alex, McFarron, Manzo, Cummings & Mehler, Ltd.

(57) ABSTRACT

Preparation of a fluorine-containing organic compound by reacting a haloalkene with hydrogen fluoride wherein both the fluorine-containing organic compound and the haloalkene separately form azeotropes with hydrogen fluoride and wherein the haloalkene/hydrogen fluoride azeotrope is more volatile than the fluorine-containing organic compound/hydrogen fluoride azeotrope.

7 Claims, 4 Drawing Sheets

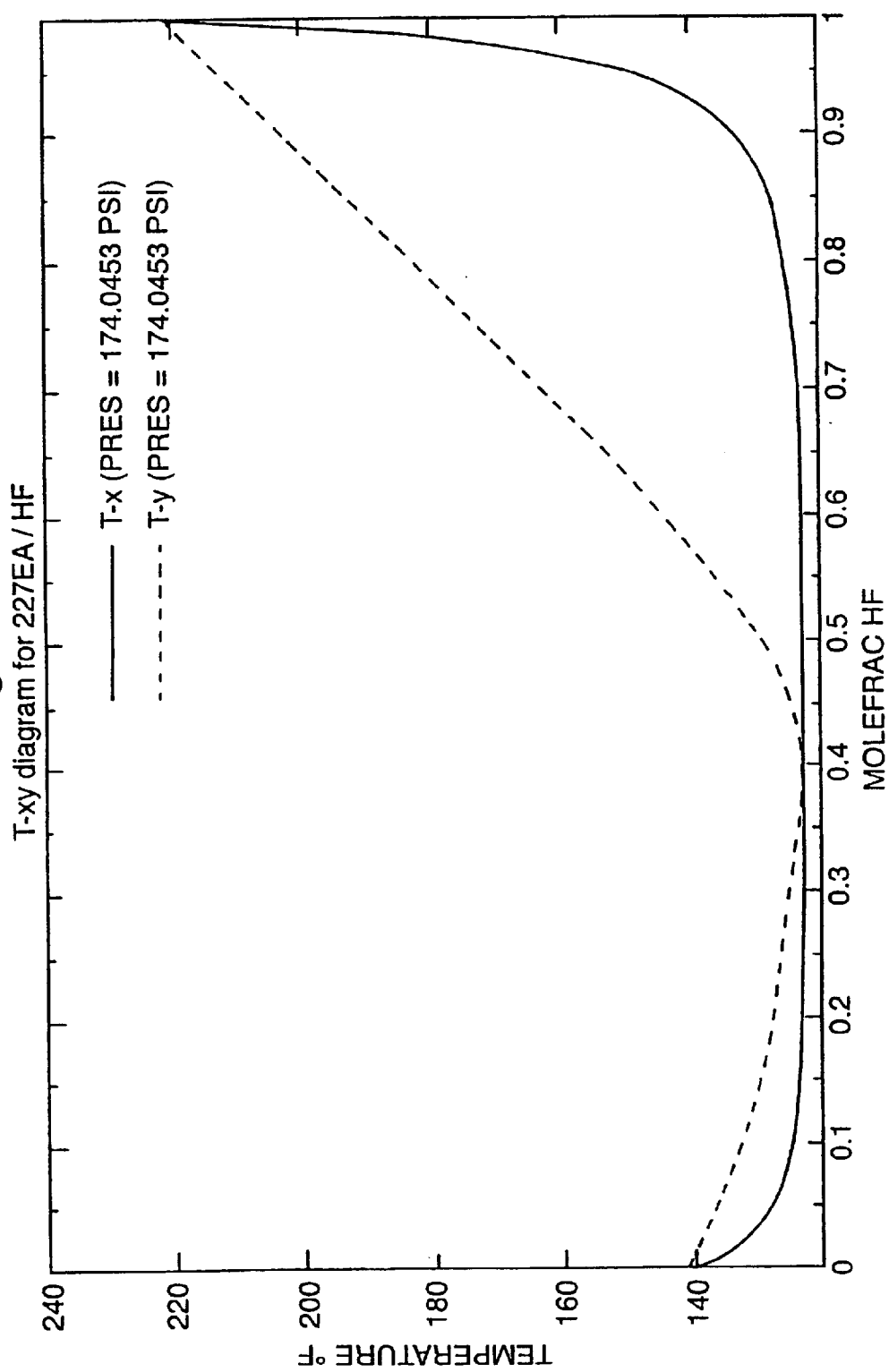

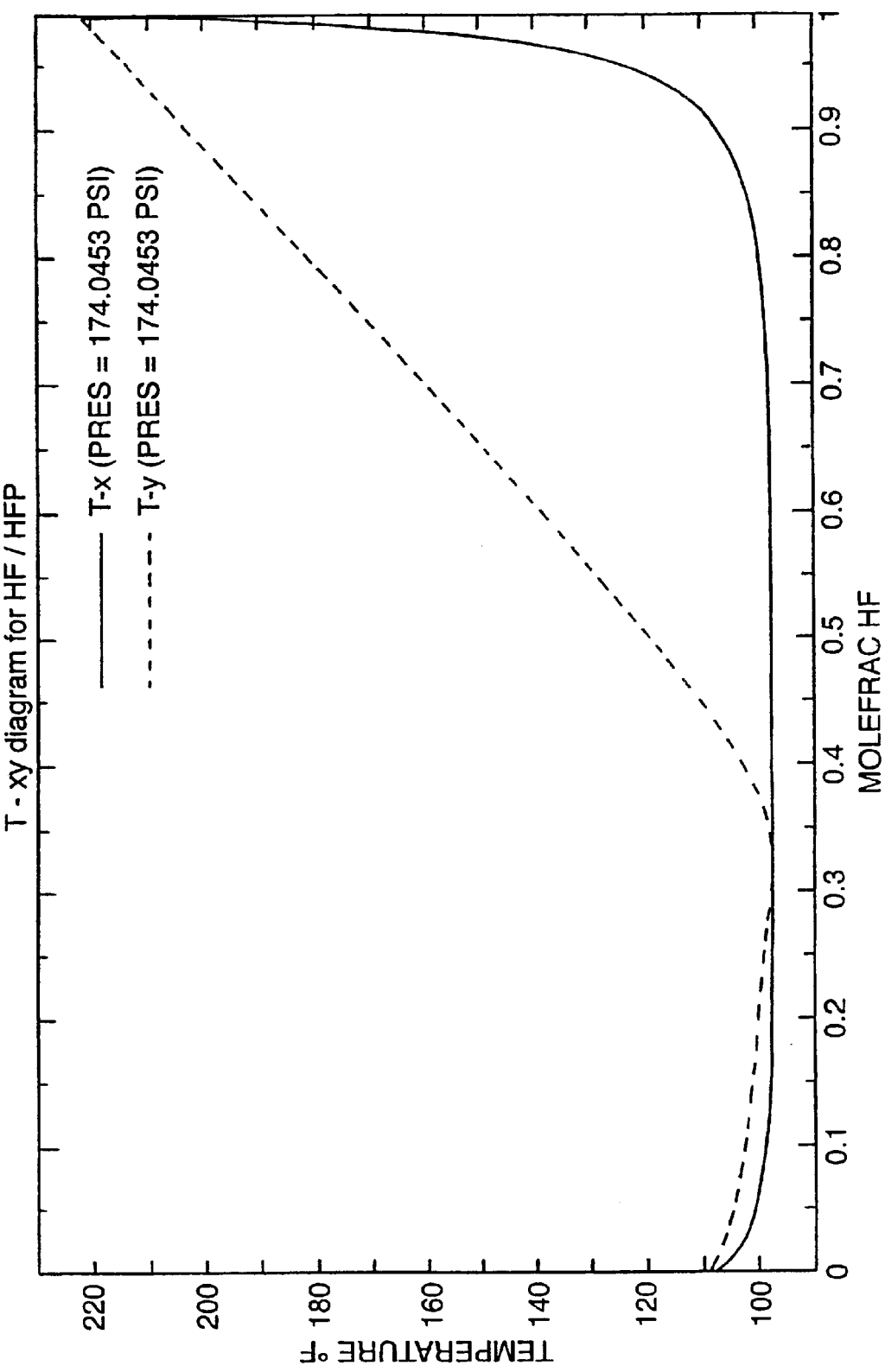

PREPARATION OF FLUORINE-CONTAINING ORGANIC COMPOUNDS

This application claims priority from provisional appl. Ser. No. 60/066836, filed Nov. 25, 1997.

The present invention relates to a process for the preparation of fluorine-containing organic compounds by reacting a haloalkene with hydrogen fluoride, particularly to a process for the preparation of hydrofluorocarbons from fluoroalkenes, more particularly to a process for the preparation of 1,1,1,2,3,3,3-heptafluoropropane from hexafluoropropene, azeotropes or azeotrope-like mixtures of a hydrofluorocarbonthydrogen fluoride, particularly azeotropes or azeotrope-like mixtures of 1,1,1,2,3,3,3-heptafluoropropane/hydrogen fluoride and azeotropes or azeotrope-like mixtures of a haloalkene/hydrogen fluoride, particularly azeotropes or azeotrope-like mixtures of hexafluoropropene/hydrogen fluoride.

Hydrofluorocarbons are widely used as replacements for chlorofluorocarbon compounds in a variety of applications. Such applications include use in medical applications, for example as an aerosol propellant, use as a fire suppressant, use in refrigeration applications and in other applications. 1,1,1,2,3,3,3-heptafluoropropane, which is known in the art as Hydrofluorocarbon 227ea and will hereinafter be referred to as "HFC 227ea" for convenience, has zero ozone depletion potential and is particularly beneficial in medical applications in the light of its combination of properties including low toxicity, non-flammability, solvent properties and boiling point.

It is known to produce hydrofluorocarbons by the hydrofluorination of a fluoroalkene to the corresponding hydrofluoroalkane, optionally in the presence of a catalyst, in the liquid phase or vapour phase. Hydrogen fluoride is known for use as a hydrofluorination agent in such hydrofluorination processes.

A variety of materials may be employed as catalysts in such hydrofluorination processes.

For example, in the vapour phase reaction of fluoroalkenes with hydrogen fluoride for the preparation of hydrofluorocarbons, eg HFC 227ea from hexafluoropropene, DE 2712732 and GB 902590 disclose the use of a chromium oxyfluoride catalyst and an activated carbon catalyst respectively.

For example, in the liquid phase reaction of fluoroalkenes with hydrogen fluoride for the preparation of hydrofluorocarbons, eg HFC 227ea from hexafluoropropene, WO 97/11042 and WO 96/0243 disclose the use of catalysts comprising an organic amine complexed with hydrogen fluoride and certain antimony catalysts respectively.

The disclosures in the aforementioned patent specifications are incorporated herein by way of reference.

A stoichiometric excess of hydrogen fluoride to fluoroalkene is normally employed in the aforementioned processes and the degree of conversion of fluoroalkene to hydrofluorocarbon is dependent on inter alia the catalyst employed, if any, and the conditions in the reactor, etc.

The product from such reactions typically comprises the desired fluorine-containing organic compound, organic by-products and hydrogen fluoride. For example, where the haloalkene is hexafluoropropene, which will hereinafter be referred to as "HFP" for convenience, the product stream leaving the reactor in which HFP is reacted with hydrogen fluoride typically contains HFC 227ea, HFP, hydrogen fluoride and azeotropes thereof.

It is normal practice to recover as much as possible of the hydrogen fluoride from the product stream from such hydrofluorination reactions for re-use. This may be partially achieved by distillation. However, the presence in the product stream of an azeotrope or azeotrope-like mixture of HFC 227ea/hydrogen fluoride and an azeotrope or azeotrope-like mixture of HFP/hydrogen fluoride limits the extent to which hydrogen fluoride can be separated from the fluoro-organic compounds by simple distillation.

It is known that the stream comprising the hydrofluorocarbonriydrogen fluoride azeotrope, eg HFC 227ea/hydrogen fluoride azeotrope, and the halo alkene/hydrogen fluoride azeotrope, eg HFP/hydrogen fluoride azeotrope, after recovery of a portion of the hydrogen fluoride by distillation, can be water-washed to allow recovery of both a mixture of organic compounds essentially free of hydrogen fluoride and aqueous hydrogen fluoride. However, such a treatment is wasteful of hydrogen fluoride since it is normal practice for aqueous hydrogen fluoride generated in this way to be neutralised with caustic solution and/or lime and ultimately disposed of.

Alternatively, the product stream from the reaction of a haloalkene with hydrogen fluoride, after recovery of a portion of the hydrogen fluoride by distillation, may be treated with a solution of alkali metal dissolved in anhydrous hydrogen fluoride as described in our patent specification WO 97/13179. However, although such a process recovers hydrogen fluoride for re-use within the process, it has the disadvantage of requiring additional equipment.

Furthermore, it is known that in the preparation of fluorine-containing organic compounds by the reaction of a haloalkene with hydrogen fluoride the haloalkene/hydrogen fluoride azeotrope can be separated from the fluorine-containing compound/hydrogen fluoride azeotrope by fractional distillation and hydrogen fluoride can be removed from the fluorine-containing organic compound/hydrogen fluoride azeotrope by treatment with water. However, treatment of the fluorine-containing organic compound/hydrogen fluoride azeotrope with water to remove hydrogen fluoride therefrom involves the use of expensive equipment and is wasteful of hydrogen fluoride.

It will be appreciated that whereas aqueous scrubbing is an effective way of removing hydrogen fluoride from the organic compound(s) after reacting hydrogen fluoride with a haloatkene aqueous scrubbing tends to be expensive in terms of hydrogen fluoride loss from the process. Preferably as much as possible, more preferably essentially all, of the hydrogen fluoride is separated from the product stream before aqueous scrubbing and particularly more preferably aqueous scrubbing is avoided.

Where in the preparation of a fluorine-containing organic compound by the reaction of a haloalkene with hydrogen fluoride the haloalkene/hydrogen fluoride azeotrope is more volatile, ie has a lower boiling point, than the fluorine-containing organic compound/hydrogen fluoride azeotrope produced in the reaction we have now found that by (a) charging the reaction product to a distillation column, (b) introducing the haloalkene into the distillation column and (c) distilling the resulting mixture both the fluorine-containing organic compound substantially free of hydrogen fluoride and the haloalkene/hydrogen fluoride azeotrope can be separated.

The separated haloalkene/hydrogen fluoride azeotrope can be recycled to the reaction vessel, can be used in another reaction or preferably at least a portion thereof is separated into a haloalkene-rich liquid phase and a hydrogen fluoride-rich liquid phase as is hereinafter more fully described.

According to the first aspect of the present invention there is provided a process for the preparation of a fluorine-containing organic compound by reacting a haloalkene with hydrogen fluoride wherein both the fluorine-containing organic compound and the haloalkene separately form azeotropes with hydrogen fluoride and wherein the haloalkene/hydrogen fluoride azeotrope is more volatile than the fluorine-containing organic compound/hydrogen fluoride azeotrope characterised by the Steps of:

A. charging the haloalkene and the mixture comprising the fluorine-containing organic compound/hydrogen fluoride azeotrope, or azeotrope-like mixture, and optionally the haloalkene/hydrogen fluoride azeotrope, or azeotrope-like mixture, and/or hydrogen fluoride arising from the reaction of the haloalkene with hydrogen fluoride to a distillation column B. recovering the haloalkene/hydrogen fluoride azeotrope, or azeotrope-like mixture, and the fluorine-containing organic compound from the distillation column separately; and C. optionally separating at least a portion of the haloalkene/hydrogen fluoride azeotrope, or azeotrope-like mixture, recovered from Step B into a haloalkene-rich liquid phase and a hydrogen fluoride-rich liquid phase.

The reaction of haloalkene with hydrogen fluoride mentioned in Step A of the process according to the first aspect of the present invention may be carried out in the liquid phase or in the vapour phase, optionally in the presence of a suitable catalyst.

Where Step C in the process according to the first aspect of the present invention is carried out separation is typically effected by allowing the haloalkene-rich liquid phase and the hydrogen fluoride-rich liquid phase to separate under gravity.

In a first embodiment of the process according to the first aspect of the present invention, the product of the reaction of the haloalkene with hydrogen fluoride is typically distilled to recover a portion of the hydrogen fluoride therefrom before the mixture comprising fluorine-containing organic compound/hydrogen fluoride azeotrope or azeotrope-like mixture thereof, haloalkene/hydrogen fluoride azeotrope or azeotrope-like mixture thereof, and hydrogen fluoride is charged to the distillation column in Step A.

The portion of hydrogen fluoride recovered by distillation prior to Step A, where it is recovered, may be recycled to the reactor vessel.

In a second embodiment of the process according to the first aspect of the present invention, the product of the reaction of the haloalkene with hydrogen fluoride is charged directly to the distillation column in Step A.

Any hydrogen fluoride which is present in excess of that required to form azeotropes in the fluorine-containing organic compound recovered from Step B may be recovered, for example by distillation.

The haloalkene/hydrogen fluoride azeotrope, or azeotrope-like mixture thereof, recovered from Step B may be fed directly to the reactor in which the fluorine-containing organic compound is produced or to an appropriate process stream(s) thereto containing the haloalkene, for example a stream containing the mixture of the haloalkene and hydrogen fluoride.

Likewise, where Step C is carried out, the hydrogen fluoride-rich phase and/or the haloalkene-rich phase recovered therefrom, may be fed directly to the reactor in which the fluorine-containing organic compound is produced or to an appropriate process stream(s) thereto containing the haloalkene, for example a stream containing the mixture of the haloalkene and hydrogen fluoride.

According to the second aspect of the present invention there is provided a process for the preparation of a fluorine-containing organic compound by reacting a haloalkene with hydrogen fluoride wherein both the fluorine-containing organic compound and the haloalkene separately form azeotropes with hydrogen fluoride and wherein the haloalkene/hydrogen fluoride azeotrope is more volatile than the fluorine-containing organic compound/hydrogen fluoride azeotrope which process comprises the steps of:

A. charging a mixture comprising a haloalkene and hydrogen fluoride to a reactor; and B. optionally recovering at least a portion of hydrogen fluoride from the reaction products from Step A by distillation characterised by the further Steps of:

C. charging the haloalkene and the mixture comprising the fluorine-containing organic compound/hydrogen fluoride azeotrope, or azeotrope-like mixture thereof, the haloalkene/hydrogen fluoride azeotrope, or azeotrope-like mixture thereof, and HF from the reactor in Step A or, where Step B is carried out, the haloalkene and the mixture comprising the fluorine-containing organic compound/hydrogen fluoride azeotrope, or azeotrope-like mixture thereof, and the haloalkene/hydrogen fluoride azeotrope, or azeotrope-like mixture thereof, from Step B to a distillation column;

D. recovering a haloalkene/hydrogen fluoride azeotrope, or azeotrope-like mixture thereof, from the distillation column in Step C;

E. recovering the fluorine-containing organic compound substantially free from hydrogen fluoride from the distillation column in Step C; and F. optionally separating at least a portion of the haloalkene/hydrogen fluoride azeotrope, or azeotrope-like mixture thereof, recovered in Step D into a haloalkene-rich phase and a hydrogen fluoride-rich phase.

In the process according to the second aspect of the present invention, where Step F is carried out: the hydrogen fluoride-rich liquid phase can be recycled to a reaction vessel for the reaction of haloalkene with hydrogen fluoride or to a feed line thereto; and at least a portion of the haloalkene-rich liquid phase can be recycled to Step C.

In the process according to the second aspect of the present invention the haloalkene/hydrogen fluoride azeotrope, or azeotrope-like mixture thereof, recovered from the distillation column in Step D or the portion thereof not subjected to Step F, where Step F is carried out, may be recycled to the reaction vessel for the reaction of haloalkene and hydrogen fluoride or to a feed-line thereto.

According to a further aspect of the present invention there is provided an azeotrope, or azeotrope-like mixture, of HFC 227ea and hydrogen fluoride.

According to a yet further aspect of the present invention there is provided an azeotrope, or azeotrope-like mixture, of HFP and hydrogen fluoride.

Where HFC 227ea is prepared by reacting HFP with hydrogen fluoride in the process according to the second aspect of the present invention and where Step A is carried out in the liquid phase in the presence of a catalyst, eg $TaF_5$, $NbF_5$ or $SbF_5$, it is suitably carried out at a temperature in the range 20 to 200° C., preferably 40 to 120° C. and especially 50 to 100° C. Suitably the reaction in Step A is carried out at superatmospheric pressure such that the reactants are in the liquid phase for sufficient time to react to produce HFC 227ea. Preferably the pressure is at least 5 bar and more preferably the pressure is 10 to 50 bar.

The residence time in the reactor in Step A in the process according to the second aspect of the present invention is sufficient to permit conversion of haloalkene feedstock into fluorine-containing organic compound. The required residence time will be dependent on inter alia the degree of conversion required, the reactant ratio and the reaction conditions.

Haloalkene from Step F in the process according to the second aspect of the present invention is preferably recycled to the reactor in which the fluorine-containing organic compound is produced.

Where a low conversion rate of haloalkene into the fluorine-containing organic compound is desired it is preferable that the feedstocks be recycled to increase the yield of the fluorine-containing organic compound from the starting material. However, we do not exclude the possibility that recycling is employed where high single pass conversions are required.

In Step A of the process according to the second aspect of the present invention the molar ratio of hydrogen fluoride (HF) to haloalkene fed to the reactor is suitably at least 1:1 and preferably 1.2 to 10:1. If a lower conversion rate is required a molar ratio of HF to haloalkene of 0.1 up to 1:1 may be employed.

In Step A of the process according to the second aspect of the present invention the molar ratio of haloalkene to the catalyst is suitably not more than 100:1 and is preferably 1 to 50:1.

The levels of HF, haloalkene and catalyst in Step A of the process according to the second aspect of the present invention are suitably selected such that the catalyst and reactants remain dissolved in the liquid phase under the reaction conditions employed.

The process according to the second aspect of the invention may be operated in batch or continuous mode as desired. Semi-batch operation may also be employed in which one or more feedstocks are fed continuously to the process and one or more other feedstocks are fed to the process in batch-wise fashion.

Alternatively, the process according to the second aspect of the present invention may be carried out in the vapour phase. Suitable conditions and catalysts for use in carrying out the process according to the second aspect of the present invention in the vapour phase are more fully described in DE 2712732 and GB 902590 mentioned hereinbefore.

In Step C of the process according to the second aspect of the present invention and in Step A of the process according to the first aspect of the present invention the haloallcene and the mixture comprising fluorine-containing organic compound/hydrogen fluoride azeotrope, or azeotrope-like mixture thereof, haloalkene/hydrogen fluoride azeotrope, or azeotrope-like mixture thereof are preferably simultaneously charged to the distillation column, and more preferably the haloalkene is charged to the distillation column at a point thereon below the point at which the mixture is charged thereto.

The process according to the first or second aspect of the present invention is applicable to mixtures of hydrogen fluoride with any haloalkene and any fluorine-containing organic compound provided that the relative volatility of the haloalkene/hydrogen fluoride azeotrope, or azeotrope-like mixture thereof, is higher than that of the fluorine-containing organic compound/hydrogen fluoride azeotrope, or azeotrope-like mixture thereof. Most hydrofluorocarbons, hydrochlorofluorocarbons and hydrofluoroethers form azeotropes or azeotrope-like mixtures, or azeotrope-like mixtures, with hydrogen fluoride and the treatment of such mixtures is a preferred embodiment of the invention, especially the treatment of mixtures wherein the fluorine-containing organic compound is a hydrofluorocarbon, a hydrochlorofluorocarbon, a chlorofluorocarbon or a hydrofluoroether.

As examples of classes of fluorine-containing organic compounds which may be prepared by the process according to the first aspect of the present invention may be mentioned inter alia hydrofluorocarbons (HFCs), eg pentafluoroethane and tetrafluoroethane, and hydrochloro-fluorocarbons (HCFCs), eg 1,1,1,2-tetrafluoro-2-chloroethane.

As examples of fluorine-containing organic compounds which may be prepared by the process according to the first aspect of the present invention may be mentioned inter alia 1,1,2-tetrafluoroethane [HFC 134a], chloro-1,1,1-trifluoroethane [HCFC 133a], chlorotetrafluoroethane [HCFC 124/124a], pentafluoroethane [HFC 125], 1,1-difluoroethane [HFC 152a], 1,1,1-trifluoroethane [HFC 143a] and 1,1,1,3,3-pentafluoropropane [HFC 245fa].

Where the fluorine-containing organic compound prepared by the process according to the first aspect of the present invention is a hydrofluorocarbon, hydrochlorofluorocarbon or chlorofluorocarbon it will usually contain from 1 to 6 carbon atoms and preferably from 1 to 4 carbon atoms.

The present invention will be further illustrated by reference to the accompanying drawings which illustrate, by way of example only, schematic representations of plants for carrying out the process according to the present invention or temperature/composition plots for certain binary systems.

In the drawings:

FIGS. 1, 2, 3 and 4 are schematic representations of plants for carrying out the process according to the second aspect of the present invention in which FIG. 1 illustrates the use of Steps A, B, C, D and E, FIG. 2 illustrates the use of Steps A, B, C, D, E and F, FIG. 3 illustrates the use of Steps A, C, D and E and FIG. 4 illustrates the use of Steps A, C, D, E and F;

FIG. 6 is a temperature/composition plot for the HFC 227ea/HF binary; and

FIG. 7 is a temperature/composition plot for the HFP/HF binary.

Although the processes according to the first and second aspects of the present invention are applicable to any of the aforementioned organic compounds they will be described hereinafter by reference to the preparation of HFC 227ea.

Figure 1:
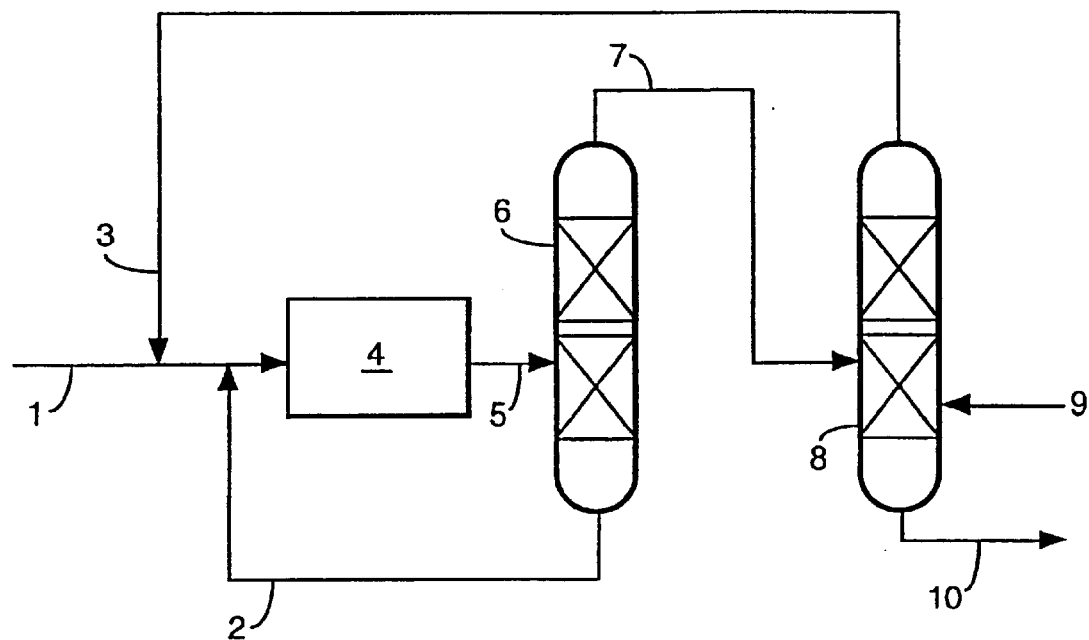
Figure 2:
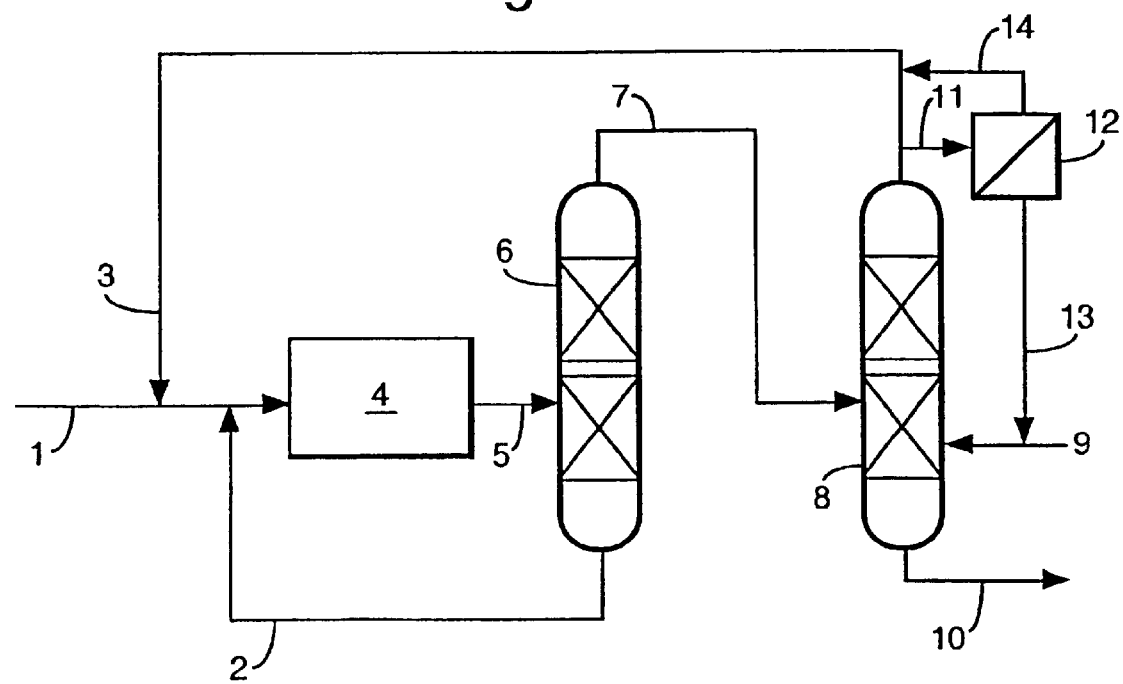

In FIGS. 1 and 2, feed pipe (1) leads to a reactor (4), which optionally contains a fluorination catalyst. Product pipe (5) from the reactor (4) is in fluid-flow communication with a first distillation column (6), which is for example a single stage flash vessel. Distillation column (6) is typically operated at a pressure of 12 bars with a bottoms temperature of 70° C. and a tops temperature of around 50° C. Bottoms pipe (2) from distillation column (6) is in fluid-flow communication with feed-pipe (1). Tops line (7) from distillation column (6) is in fluid-flow communication with a second distillation column (8), which is for example a packed column. Distillation column (8) is typically operated at a pressure of around 12 bars with a tops temperature of 37° C and a bottoms temperature of around 60° C. Distillation column (8) is provided with a feed line (9) below the point at which tops line (7) is attached to it, a bottoms pipe (10) and a tops pipe (3) which is in fluid-flow communication with feed-pipe (1).

In FIG. 2, tops pipe (3) from distillation column (8) is provided with a line (11) which is in fluid flow communication with phase separator (12). Phase separator (12) is provided with a line (13) in fluid-flow communication with feed line (9) and a line (14) in fluid-flow communication with tops line (3).

In operation, the reactor (4) is charged through feed pipe (1) with a feed stream containing fresh hydrogen fluoride, recycled hydrogen fluoride (from bottoms line (2) and tops line (3)) and HFP/hydrogen fluoride azeotrope (from tops line (3)). The product from reactor (4) (HFC 227ea, hydrogen fluoride and optionally unconverted HFP) travels through product pipe (5) to the first distillation column (6). In distillation column (6), hydrogen fluoride, which is recycled via bottoms line (2) to feed pipe (1), is separated from the mixture of HFC 227ea, hydrogen fluoride and unconverted HFP. The mixture of HFC 227ea, residual hydrogen fluoride and HFP is fed via tops line (7) from the distillation column (6) to the second distillation column (8). HFP is fed via feed line (9) to column (8). A stream comprising HFP and essentially all the hydrogen fluoride content of the stream entering distillation column (8) via line (7) is removed from the top of distillation column (8) via line (3) and the product stream HFC 227ea is removed from the bottom of column (8) via bottoms lead (10).

Preferably, as shown in FIG. 2, a portion of the stream in pipe (3) is diverted in the liquid phase through pipe (11) to separator (12) in which a HFP-rich phase is separated from an hydrogen fluoride-rich phase. The HFP-rich liquid phase is fed via line (13) to feed line (9) to distillation column (8). The hydrogen fluoride-rich liquid phase from separator (12) is returned via line (14) to tops pipe (3) to feed line (1).

Figure 3:
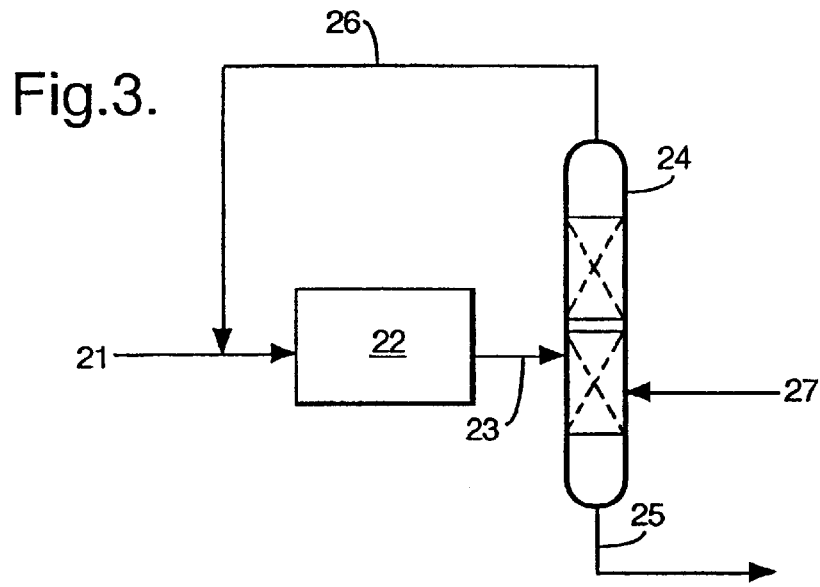
Figure 4:
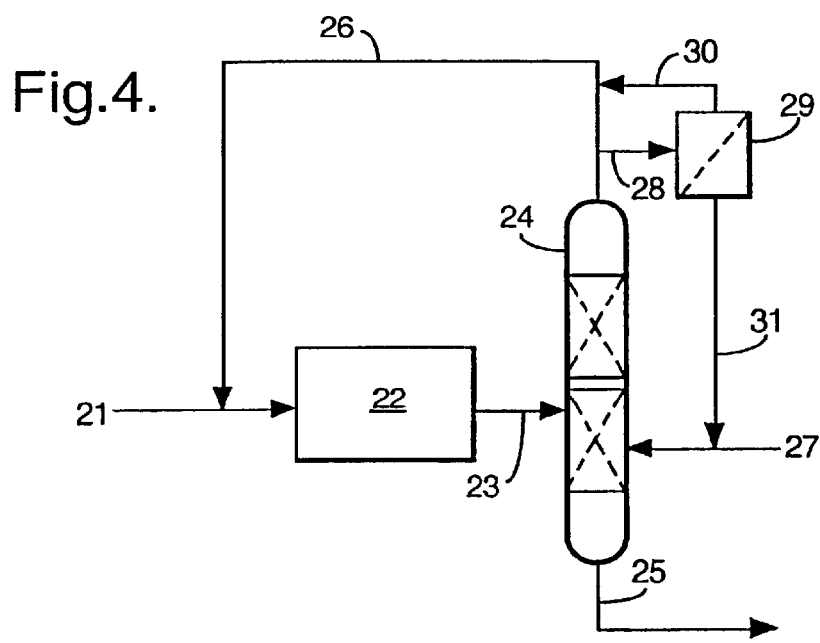

In FIGS. 3 and 4, feed pipe (21) leads to a reactor (22), which optionally contains a fluorination catalyst. Product pipe (23) from the reactor (22) is in fluid-flow communication with a distillation column (24), which is for example a packed column. Distillation column (24) is typically operated at a pressure of around 12 bars with a tops temperature of 37° C. and a bottoms temperature of around 60° C. Distillation column (24) is provided with a bottoms pipe (25), a tops pipe (26), which is in fluid-flow communication with feed-pipe (21), and feed line (27) below the point at which product pipe (23) is attached to it.

In FIG. 4, tops pipe (26) from distillation column (24) is provided with a line (28) which is in fluid flow communication with phase separator (29). Phase separator (29) is provided with both line (30) in fluid-flow communication with line (26) and line (31) in fluid-flow communication with feed line (27).

In operation, the reactor (22) is charged through feed pipe (21) with a feed stream containing hydrogen fluoride (fresh and recycled through a hydrogen fluoride-rich stream (from line (26)) and recycled HFP. The product from separator (29) (HFC 227ea, hydrogen fluoride and optionally unconverted HFP) travels through product pipe (23) to distillation column (24). HFP is fed via feed line (27) to column (24). A stream comprising HFP and essentially all the hydrogen fluoride content of the stream entering distillation column (24) via line (23) is removed from the top of distillation column (24) via line (26) and the product stream HFC 227ea is removed from the bottom of column (24) via bottoms lead (25).

Preferably, as shown in FIG. 4, a portion of the stream in pipe (26) is diverted in the liquid phase through pipe (28) to separator (29) in which a HFP-rich phase is separated from a hydrogen fluoride-rich phase. The HFP-rich phase from column (24) is fed via line (31) to feed line (27) to distillation column (24). The hydrogen fluoride-rich phase from separator (29) is returned via lines (30) and (26) to feed line (21).

Figure 5:
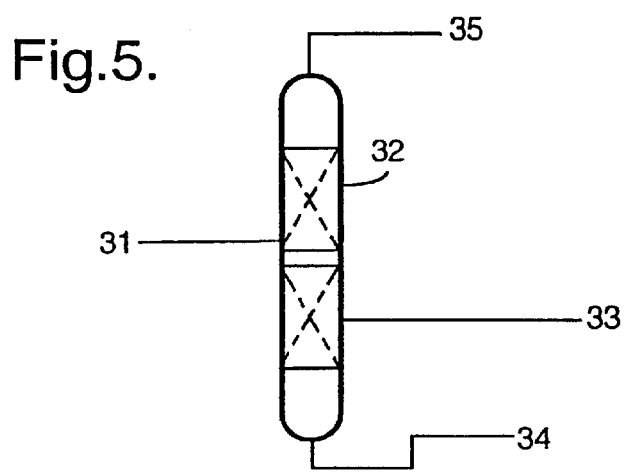
FIG. 5 is a schematic representations of a plant for carrying out the second embodiment of the process according to the first aspect of the present invention.

In FIG. 5, distillation column (32) is provided with feed line (31) connected to a reactor (not shown), feed line (33), bottom line (34) and top line (35). In operation, a mixture comprising HFC 227ea/HF azeotrope, or azeotrope-like mixture, HFP/HF azeotrope, or azeotrope-like mixture and/or HF is fed via line (31) to distillation column (32) and a stream comprising HFP is fed via line (33) to distillation column (32). HFP/HF azeotrope, or azeotrope-like mixture, is removed from distillation column (32) via top line (35) and HFC 227ea substantially free from HF is removed from distillation column (32) via bottom line (34).

The present invention is further illustrated by reference to the following Example.

EXAMPLE

The Example reveals that both HFP and HFC 227ea form azeotropes with HF and, at constant pressure the boiling point of he HFP/HF azeotrope is lower than the boiling point of the HFC 227ea/HF azeotrope.

A temperature/composition plot for the HFC 227ea/HF binary is illustrated in FIG. 6 wherein the dashed line—represents the vapour phase composition and the solid line represents the liquid phase composition. From FIG. 6 it can be seen that at 174 psi the HFC 227ea/HF azeotrope has a boiling point of 123° F. and a composition of 42 mole% HF and 58 mole% HFC 227ea.

A temperature/composition plot for the HFP/HF binary is illustrated in FIG. 7 wherein the dashed line—represents the vapour phase composition and the solid line represents the liquid phase composition. From FIG. 7 it can be seen that at 174 psi the HFP/HF azeotrope has a boiling point of 98° F. and a composition of 38 mole% HF and 62 mole% HFP.

What is claimed is:

1. A process for the preparation of a fluorine-containing organic compound by reacting a haloalkene with hydrogen fluoride
    wherein both the fluorine-containing organic compound and the haloalkene separately form azeotropes, or azeotrope-like mixtures, with hydrogen fluoride and wherein the haloalkene/hydrogen fluoride azeotrope, or azeotrope-like mixture thereof, is more volatile than the fluorine-containing organic compound/hydrogen fluoride azeotrope, or azeotrope-like mixture thereof, characterised by the Steps of:
    A. charging the haloalkene and the mixture comprising the fluorine-containing organic compound/hydrogen fluoride azeotrope, or azeotrope-like mixture and optionally the haloalkene/hydrogen fluoride azeotrope, or azeotrope-like mixture and/or hydrogen fluoride, arising from the reaction of the haloalkene with hydrogen fluoride to a distillation column; and
    B. recovering the haloalkene/hydrogen fluoride azeotrope, or azeotrope-like mixture, and the fluorine-containing organic compound from the distillation column separately.

2. A process as claimed in claim 1 further characterised by the step of separating at least a portion of the haloalkene/ hydrogen fluoride azeotrope, or azeotrope-like mixture, recovered from Step B into a haloalkene-rich liquid phase and a hydrogen fluoride-rich liquid phase.

3. A process for the preparation of a fluorine-containing organic compound by reacting a haloalkene with hydrogen fluoride
    wherein both the fluorine-containing organic compound and the haloalkene separately form azeotropes, or azeotrope-like mixtures, with hydrogen fluoride and wherein the haloalkene/hydrogen fluoride azeotrope, or azeotrope-like mixture thereof, is more volatile than the fluorine-containing organic compound/hydrogen fluoride azeotrope, or azeotrope-like mixture thereof, which comprises the step of:

A. charging a mixture comprising a haloalkene and hydrogen fluoride to a reactor; and B. optionally recovering at least a portion of hydrogen fluoride from the reaction products from the reactor in Step A by distillation characterised by the further Steps of:

C. charging the haloalkene and the mixture comprising the fluorine-containing organic compound/hydrogen fluoride azeotrope, or azeotrope-like mixture thereof, the haloalkene/hydrogen fluoride azeotrope, or azeotrope-like mixture thereof, and HF from the reactor in Step A or, where Step B is carried out, the haloalkene and the mixture comprising the fluorine-containing organic compound/hydrogen fluoride azeotrope, or azeotrope-like mixture thereof, and the haloalkene/hydrogen fluoride azeotrope, or azeotrope-like mixture thereof, from Step B to a distillation column;

D. recovering a haloalkene/hydrogen fluoride azeotrope, or azeotrope-like mixture thereof, from the distillation column in Step C; and E. recovering the fluorine-containing organic compound substantially free from hydrogen fluoride from the distillation column in Step C.

4. A process as claimed in claim 3 characterised by the further step of separating at least a portion of the haloalkene/hydrogen fluoride azeotrope, or azeotrope-like mixture thereof, recovered in Step D into a haloalkene-rich phase and a hydrogen fluoride-rich phase.

5. A process as claimed in claim 1 or 3 wherein the fluorine-containing organic compound is a hydrofluorocarbon and the haloalkene is a fluoroalkene.

6. A process as claimed in claim 5 wherein the hydrofluorcarbon is HFC 227ea and the fluoroalkene is HFP.

7. A process as claimed in claim 3 wherein the haloalkene-rich phase from Step F is returned to the distillation column in Step C and the hydrogen fluoride-rich phase from Step F is recycled to the reactor in Step A.

* * * * *